United States Patent

Fukui et al.

[11] Patent Number: 5,308,314
[45] Date of Patent: May 3, 1994

[54] INTEGRATED HEART-LUNG MACHINE

[75] Inventors: Yasuhiro Fukui, 14-13, 3-chome, Kanamecho, Toshima-ku, Tokyo; Akio Funakubo, Sagamihara; Katsumi Takahashi, 771-56, Ouazakounosu, Koga-shi, Ibaraki Pref.; Hiroshi Sasagawa, Koga; Hikaru Nakanishi, Tokyo, all of Japan

[73] Assignees: Yasuhiro Fukui, Tokyo; Katsumi Takahashi, Koga, both of Japan

[21] Appl. No.: 944,086

[22] Filed: Sep. 11, 1992

[30] Foreign Application Priority Data

Nov. 19, 1991 [JP] Japan .................. 3-329821

[51] Int. Cl.$^5$ .............................. A61M 37/00
[52] U.S. Cl. ........................ 604/4; 415/900; 128/DIG. 3
[58] Field of Search ............ 128/DIG. 3; 604/4, 151; 210/321.63; 261/DIG. 28; 422/45–48; 415/900

[56] References Cited

U.S. PATENT DOCUMENTS

| | | | |
|---|---|---|---|
| 3,026,871 | 3/1962 | Thomas | 422/48 X |
| 3,487,784 | 1/1970 | Rafferty et al. | 415/900 X |
| 3,674,440 | 7/1972 | Kitrilakis | 261/DIG. 28 |
| 3,771,658 | 11/1973 | Brumfield | 422/48 X |
| 3,771,899 | 11/1973 | Brumfield | 128/DIG. 3 X |
| 3,841,837 | 10/1974 | Kitrilakis | 422/48 |
| 4,790,942 | 12/1988 | Shmidt et al. | 210/321.63 |
| 4,846,152 | 7/1989 | Wampler et al. | 128/DIG. 3 |
| 5,039,482 | 8/1991 | Panzani et al. | 128/DIG. 3 |
| 5,049,134 | 9/1991 | Golding et al. | 415/900 |
| 5,217,689 | 6/1993 | Raible | 128/DIG. 3 |

FOREIGN PATENT DOCUMENTS 2-41172 2/1990 Japan .
2-12108 3/1990 Japan .

Primary Examiner—C. Fred Rosenbaum
Assistant Examiner—Frank Wilkens
Attorney, Agent, or Firm—Oblon, Spivak, McClelland, Maier & Neustadt

[57] ABSTRACT

An integrated heart-lung machine, which includes a blood pump having a casing of a cup-like shape interiorly defining a pump chamber at an intermediate portion thereof for pumping in and out blood from a blood inlet to a guide flange formed at opposite ends of the casing; a rotor having a rotary member securely fixed to the fore end thereof within the pump chamber and journalled in the guide flange; an artificial lung of a doughnut-like or cylindrical shape connected contiguously to a blood flow passage in the guide flange and concentrically with the rotor; a stator detachably fitted in an intermediate portion between the rotor and the artificial lung; and a pedestal base located at one side of the artificial lung and provided with a blood outlet in communication with the artificial lung. Accordingly, influent blood to the pump chamber is sent into the artificial lung through the blood passage by the pumping action of the rotor, and is refreshed by contact with air or oxygen in the lung, which is maintained in a heated state by the stator, and returned to the patient's body through the blood outlet. This arrangement permits minimizing of the length of the blood circulating passages to and through the machine and permits shortening and minimizing of the blood passages interconnecting the blood pump, artificial lung and blood filter, while preventing blood contamination and leaks as well as blood cell destruction. Easy installation and handling is also permitted in a sanitary region on a bed or on an operating table.

6 Claims, 3 Drawing Sheets

INTEGRATED HEART-LUNG MACHINE

BACKGROUND OF THE INVENTION

1. Field of the Invention

This invention relates to a heart-lung machine for pumping blood out of a patient's body for blood treatment and returning the treated blood to the patient's body.

2. Description of Prior Art

Extracorporeal circulation type heart-lung machines have been known, for example, from Japanese Patent Publication H2-12108 disclosing a heart-lung machine which is composed of a series of separably connected operating units including an artificial lung unit for refreshing blood through oxidation, and a heat exchanger unit in which heated water is circulated to maintain the blood at a predetermined temperature, and also from Japanese Laid-open Patent Application H2-41172 disclosing a heart-lung machine which has a blood treating section (i.e. an artificial lung) and a blood feed mechanism integrally incorporated into outer and inner portions of a cylindrical casing, respectively, such that blood, inflowing through an apex portion of a blood guide member of a substantially conical shape, is discharged through a blood discharge port by rotation of a rotary member for introduction into the blood treating section and then being allowed to flow out through a blood outlet on the downstream side, the blood treating section being interiorly provided with a heat exchanger for circulation of a heat exchanging medium therethrough.

In the former case where the blood pump, artificial lung and heat exchanger are connected in series as separable operating units, however, the machine involves a lengthy flow passage for the blood to be treated and necessitates providing a support stand exclusively for fixedly retaining the position of the machine body. In this connection, since it is difficult to install the machine in a sanitary region in the vicinity of a patient and since the heat exchanger unit needs a separate heat source, difficulties are often encountered in reducing the volume of the blood in the feed system or the blood pumped to a marked degree, coupled with the inconvenient and troublesome job of connecting inflow and outflow tubes for the heat exchanging medium to and from the heat exchanger unit.

Further, in the latter case, blood strikes against guide blades under the influence of the centrifugal force of the pump, and, as the blood is introduced into the artificial lung at a high velocity under the guidance of the guide blades, it vigorously strikes the casing of the artificial lung at the blood inlet thereof and also against hollow yarns of the lung. It follows that the blood is susceptible to destruction of blood cells (hemolysis) due to physical stresses.

SUMMARY OF THE INVENTION

It is a primary object of the present invention to provide an integrated heart-lung machine which is easy to handle and avoids the destruction of blood cells.

It is another object of the present invention to provide an integrated heart-lung machine which can be installed at a position close to a patient or an operating table.

In accordance with the present invention, the above-stated objectives are achieved by the provision of an integrated heart-lung machine, essentially including: a blood pump having a casing of a cup-like shape interiorly defining a pump chamber in an intermediate portion thereof for pumping in and out blood from a blood inlet to a guide flange formed at opposite ends of the casing; a rotor having a rotary member securely fixed to the fore end thereof within the pump chamber and journalled in the guide flange; an artificial lung of a doughnut-like or cylindrical shape connected contiguously to a blood flow passage in the guide flange and concentrically with the rotor; a stator detachably fitted in an intermediate portion between the rotor and the artificial lung; and a pedestal base located at one side of the artificial lung and provided with a blood outlet in communication with the artificial lung.

The above and other objects, features and advantages of the invention will become apparent from the following description and the appended claims, taken in conjunction with the accompanying drawings which show by way of example preferred embodiments of the invention.

DESCRIPTION OF PREFERRED EMBODIMENTS

Figure 1:
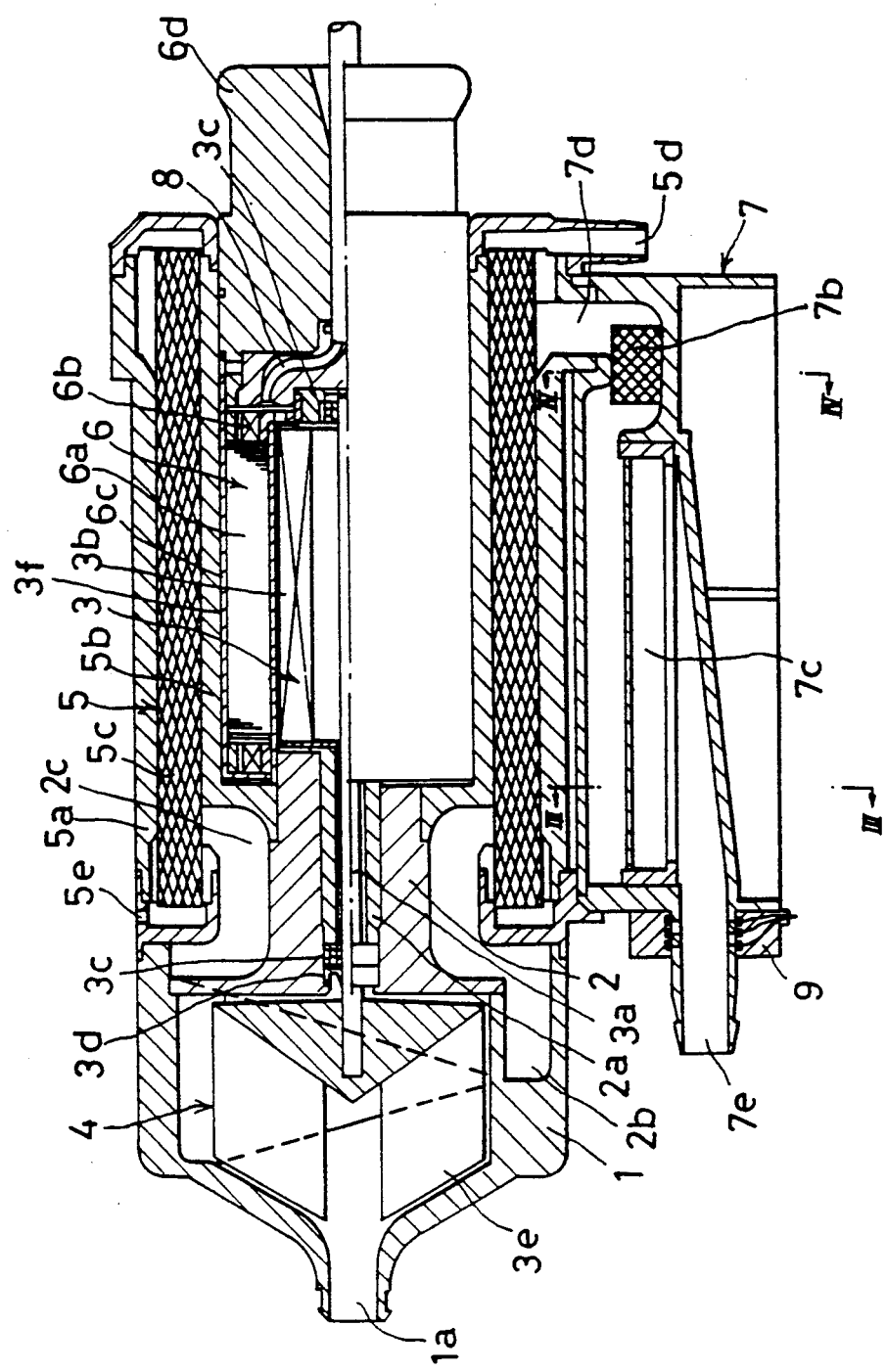
FIG. 1 is a sectional view of a first embodiment of the invention.
Figure 2:
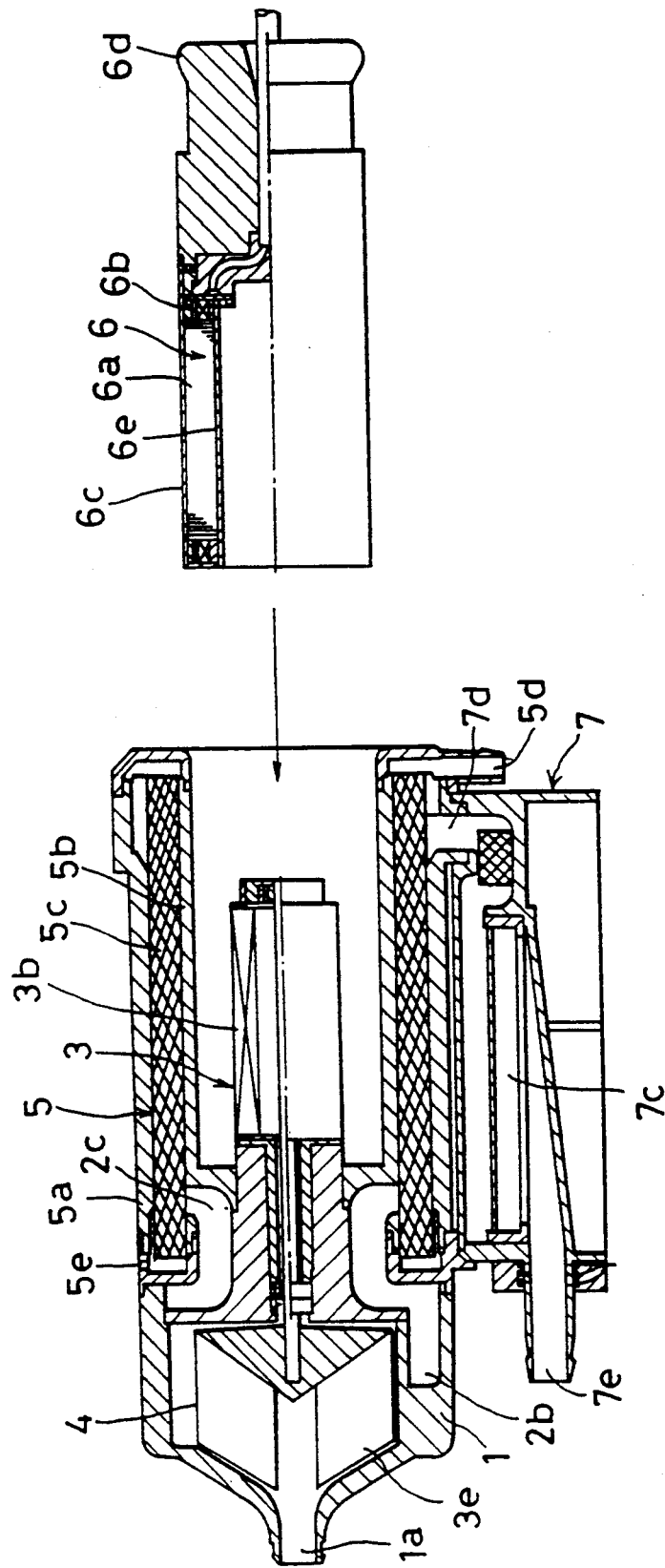
FIG. 2 is a sectional view of the heart-lung machine of the first embodiment, with the stator in a detached state.
Figure 3:
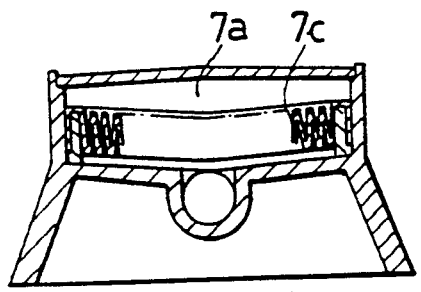
FIG. 3 is a sectional view taken along line III—III of FIG. 1.
Figure 4:
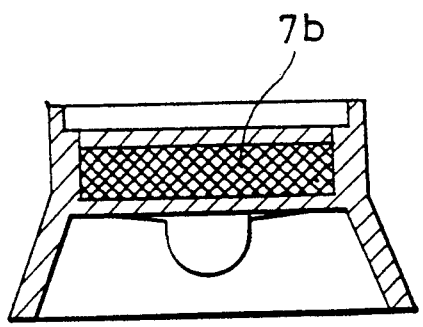
FIG. 4 is a sectional view taken along line IV—IV of FIG. 1.

Hereafter, the invention is described more particularly, firstly by way of the first embodiment shown in FIGS. 1-4.

In these figures, indicated at 1 is a casing of a cup-like shape having a blood inlet 1a projected from one end and a guide flange 2 fitted in the other end thereof. The guide flange 2 is provided with an aperture 2a axially in a center portion thereof and formed with a blood flow passage 2b and a blood chamber 2c in peripheral edge portions.

In this instance, for the purpose of securing smooth blood flow, the blood flow passage 2b is formed so as to extend helically as far as a point on the inner side of the artificial lung 5 which will be described hereinafter. The blood chamber 2c is formed coextensively around the inner periphery of an artificial lung 5.

Denoted at 3 is a rotor which is constituted by a rotational shaft 3a and a magnet 3b. The rotational shaft 3a is supported in bearings 3c and shielded by a mechanical seal 3d from a pump chamber 4 which is defined by the casing 1 and the guide flange 2. Blades 3e are fixed on the rotational shaft 3a.

Designated at 5 is the artificial lung which is provided with bundles of a multitude of porous hollow yarns 5c of polypropyrene or like material between an outer sleeve 5a, of an outer diameter substantially the same as that of the casing 1, and an inner sleeve 5b, and communicated with the blood chamber 2c. Air or oxygen inlet 5d and outlet 5e are provided at the lower and upper ends of the outer sleeve 5a, respectively.

The inner sleeve 5b is formed of a thermally conductive material such as stainless steel SUS304 or the like.

Indicated at 6 is a motor stator which is constituted by an iron core 6a and winding 6b. The iron core 6a is fixedly laminated in an outer case 6c which is securely connected to a grip member 6d by means of screws and slidable in inward and outward directions in contact with the inner surface of the inner sleeve 5b of the artificial lung 5. The outer case 6c is also formed of a thermally conductive material, for example, stainless steel SUS304 or the like.

Non-magnetic material is used for a cap-like outer wall 3f of the rotor 3 as well as for an inner wall 6e of the stator 6. The cap-like outer wall 3f is tightly fixed to the inner sleeve 5b to prevent the intrusion of bacteria from outside.

Indicated at 7 is a pedestal base of a trapezoidal shape, which is provided with a rectangular recess 7a on the top side to accommodate sponge 7b and filter 7c therein. This pedestal base 7 is further provided with blood inlet 7d and outlet 7e on its upper and lower sides, respectively. The aforementioned inlet 1a of the pump casing is located on the same side as the blood outlet 7e to facilitate the connection of tubes when the heart-lung machine is to be set on a patient.

Denoted at 8 is a lead wire and at 9 is a flow sensor which is, for example, an electromagnetic flowmeter or an ultrasonic Doppler flowmeter, and is detachably located in a tubular portion of the blood outlet 7e.

The heart-lung machine of the above-described embodiment operates in the manner described below. Firstly, the stator 6, which has been sterilized in its entirety, is fitted between the inner sleeve 5b and the outer wall 3f of the rotor 3 as indicated by an arrow in FIG. 2, and is slid into the position shown in FIG. 1. Thereafter, electric current is supplied to the lead wire 8 to produce a rotating magnetic field in the stator 6, which rotationally drives the rotor 3. As a result, the blades 3e are rotated in a predetermined direction. The influent blood from the inlet 1a is sent into the artificial lung 5 after decreasing its velocity to a sufficiently low level through the blood passage 2b and blood chamber 2c.

In this regard, since the blood passage 2b is helically shaped, the blood which is discharged from the pump chamber 4 by rotation of the blades 3e is allowed to flow smoothly through the blood passage 2b without blood cell destruction or hemolysis. As the energy of flow velocity is converted into a pressure in the blood chamber 2c to a sufficient degree, the blood is urged to flow into the artificial lung 5 smoothly from the entire inner periphery thereof in such a manner as to prevent localized blood flows in the bundles of hollow yarns 5c.

On the other hand, heat is generated by the stator 6 due to copper and iron losses and reactive power, which can be controlled through the power supply, allows for heating the outer case 6c of the stator 6 and the inner sleeve of the artificial lung 5 to a suitable temperature level, the outer case 6 and inner sleeve 5b maintaining the blood in the artificial lung 5 at a desired temperature through heat exchange with influent blood to the lung 5.

Further, the influent blood in the artificial lung 5 is brought into contact with oxygen or air, which has been introduced into the artificial lung 5 through the walls of a multitude of hollow yarns 5c, and refreshed with dissolved oxygen. The refreshed blood is discharged to the inlet 7d of the pedestal base 7b and, after removal of bubbles and thrombus at the sponge 7b and filter 7c, is returned through the blood outlet 7e.

Figure 5:
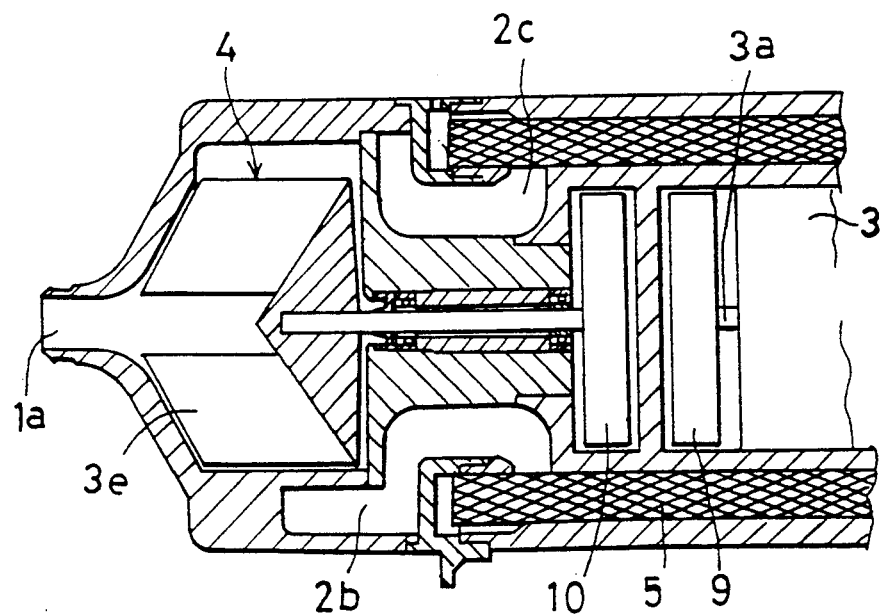
FIG. 5 is a sectional view of a second embodiment of the invention.

FIG. 5 illustrates a second embodiment of the present invention, which is provided with a magnet 9 at the fore end of the rotational shaft 3a of the rotor 3 to form a magnetic coupling in cooperation with a magnet 10 which is fixed at the inner end of the blade shaft for the pump blades 3e. This arrangement completely prevents blood leakage.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. An integrated heart-lung machine, comprising:
   a blood pump having a casing of a substantially cup-like shape, the casing having a blood inlet and a guide flange, the casing interiorly defining a pump chamber at an intermediate portion thereof for pumping in and out blood from said blood inlet to said guide flange, said guide flange having a blood flow passage formed therein;
   a rotor having a rotational shaft with rotor blades securely fixed to the fore end thereof within said pump chamber and the rotational shaft being journalled in said guide flange;
   an artificial lung having one of a substantially doughnut-like and cylindrical shape connected contiguously to said blood flow passage in said guide flange and positioned concentrically with said rotor;
   a stator detachably fitted in an intermediate portion between said rotor and said artificial lung; and
   a pedestal base located at one side of said artificial lung and provided with a blood outlet in communication with said artificial lung wherein said blood flow passage is of a helical shape and wherein said guide flange includes a blood chamber located between said rotor blades and said rotor which is communicated with said artificial lung substantially along an entire inner peripheral portion thereof and which is communicated with said blood flow passage.

2. An integrated heart-lung machine as defined in claim 1, wherein said pedestal base is provided with a filter at said blood outlet in communication with said artificial lung.

3. An integrated heart-lung machine as defined in claim 1, wherein said stator and said artificial lung include an outer sleeve and an inner sleeve of thermally conductive material, respectively, and which comprise a holder for holding said outer and inner sleeves together.

4. An integrated heart-lung machine as defined in claim 1, wherein said blood outlet is located on the same side of the machine as said blood inlet.

5. An integrated heart-lung machine as defined in claim 1, which comprises a flow sensor which is removably located in said blood outlet.

6. An integrated heart-lung machine as defined in claim 1, which comprises a filter located in said blood outlet of said pedestal base and in communication with said artificial lung.

* * * * *